United States Patent [19]

Ahern et al.

[11] Patent Number: 5,594,497
[45] Date of Patent: Jan. 14, 1997

[54] ENDOSCOPE PROVIDED WITH A DISTALLY LOCATED COLOR CCD

[76] Inventors: John M. Ahern, 644 Santa Maria La., Davidsonville, Md. 21035; Stephen Koo, 83-58 Charlecote Ridge, Jamaica, N.Y. 11432

[21] Appl. No.: 575,463

[22] Filed: Dec. 20, 1995

Related U.S. Application Data

[63] Continuation of Ser. No. 43,904, Apr. 7, 1993, abandoned.

[51] Int. Cl.⁶ .............................. A61B 1/04; A61B 1/06; H04N 7/18
[52] U.S. Cl. ................................ 348/71; 348/68
[58] Field of Search ..................... 348/71, 65, 66, 348/68; H04N 7/18

[56] References Cited

U.S. PATENT DOCUMENTS

| | | |
|---|---|---|
| Re. 33,854 | 3/1992 | Adair . |
| Re. 34,002 | 7/1992 | Adair . |
| 3,456,641 | 7/1969 | Yokota et al. . |
| 4,253,447 | 3/1981 | Moore et al. . |
| 4,618,884 | 10/1986 | Nagasaki . |
| 4,773,396 | 9/1988 | Okazaki . |
| 4,853,772 | 8/1989 | Kikuchi ................................ 348/71 |
| 4,878,485 | 11/1989 | Adair . |
| 4,895,138 | 1/1990 | Yabe . |
| 4,905,670 | 3/1990 | Adair . |
| 4,918,521 | 4/1990 | Yabe et al. . |
| 4,979,498 | 12/1990 | Oneda et al. ........................ 128/6 |
| 5,016,975 | 5/1991 | Sasaki et al. . |
| 5,026,368 | 6/1991 | Adair . |
| 5,125,395 | 6/1992 | Adair . |
| 5,143,054 | 9/1992 | Adair . |
| 5,188,094 | 2/1993 | Adair . |
| 5,228,430 | 7/1993 | Sakamoto ............................ 348/65 |
| B1 4,858,001 | 6/1992 | Milbank et al. ...................... 348/66 |

*Primary Examiner*—Howard W. Britton

[57] ABSTRACT

The present invention is directed to an endoscope provided with a color CCD chip located in the distal end of the endoscope. The CCD chip directly produces a chromatic signal which is sent to a video system center and then to a monitor for viewing.

7 Claims, 4 Drawing Sheets

ENDOSCOPE PROVIDED WITH A DISTALLY LOCATED COLOR CCD

This application is a continuation of application Ser. No. 08 / 043,904 filed on Apr. 7, 1993 now abandoned.

BACKGROUND OF THE INVENTION

1. Field of the Invention

The present invention relates to a video endoscope and, more particularly, to an endoscope provided with a charge coupled device (CCD) located at the distal end of the endoscope.

2. Prior Art

Historically, whenever a patient exhibited particular symptoms which would lead a medical practitioner to believe that these symptoms would indicate a potential problem within the patient's body, an invasive procedure had to be conducted to determine whether such a problem existed and, perhaps, to rectify this problem. These procedures necessitated that a surgeon perform major surgery in the region of interest. This surgery required a relatively long period of recuperation, generally in a hospital. The expense of these procedures, as well as the required recuperation period, were both very costly.

Recently, many devices have been developed, such as endoscopes, which would allow a surgeon or other medical practitioner to view the interior of a patient's body in a much less invasive manner. U.S. Pat. No. 3,456,641 issued to Yokota et al; U.S. Pat. No. 4,253,447 issued to Moore et al; U.S. Pat. No. 4,618,884 issued to Nagasaki; U.S. Pat. No. 4,895,138 issued to Yabe; U.S. Pat. 4,918,521 issued to Yabe et al; U.S. Pat. 4,773,396 issued to Okazaki; U.S. Pat. No. 5,016,975 issued to Sasaki et al and U.S. Pat. 5,188,094 issued to Adair are typical of these types of endoscopes.

As shown in the Yokota et al patent, a camera was provided at the distal end of the endoscope to produce a signal corresponding to the features which are in the field of view of the endoscope. Subsequently, CCD's were substituted for the camera shown in the Yokota et al patent as shown in the Okazaki and Adair patents. However, since these CCD's produced a black and white image, various methods were developed to convert these black and white images to color images. A typical system of this type is shown in the Moore et al patent in which the black and white images produced by the CCD are converted into color images downstream from the distal end of the endoscope. Unfortunately, these types of systems were quite costly, since additional processing circuitry, as well as a relatively complicated lens system, would be required.

SUMMARY OF THE INVENTION

The present invention corrects the deficiencies of the prior art by providing a video endoscopic imaging system designed to be used in the same procedures as the conventional rigid and flexible endoscopes which are currently in use. This device effectively replaces the standard rigid optical lens systems which are currently employed and substitutes a CCD chip directly producing a chromatic output, for the standard CCD chip now utilized in endoscopes which directly produces a non-chromatic output. This new CCD chip is also provided in the distal end of the endoscope. The signal produced at each point in the field of view of the endoscope of the present invention is proportional to the brightness of the color which achieves full color images. During each moment of time, the CCD according to the present invention, records a color image of the scene as it appears under that particular color of illumination and transmits it to a video system center which, in turn, feeds it to a color monitor. The color fidelity of the video image is enhanced since, throughout the entire imaging system, from the CCD sensor chip to the monitor display screen, precise control over color reproduction is established and maintained.

Additional advantages and features of the present invention will become apparent from the description of the present invention taken in conjunction with the accompanying drawings.

DETAILED DESCRIPTION OF THE PREFERRED EMBODIMENT

Figure 1:
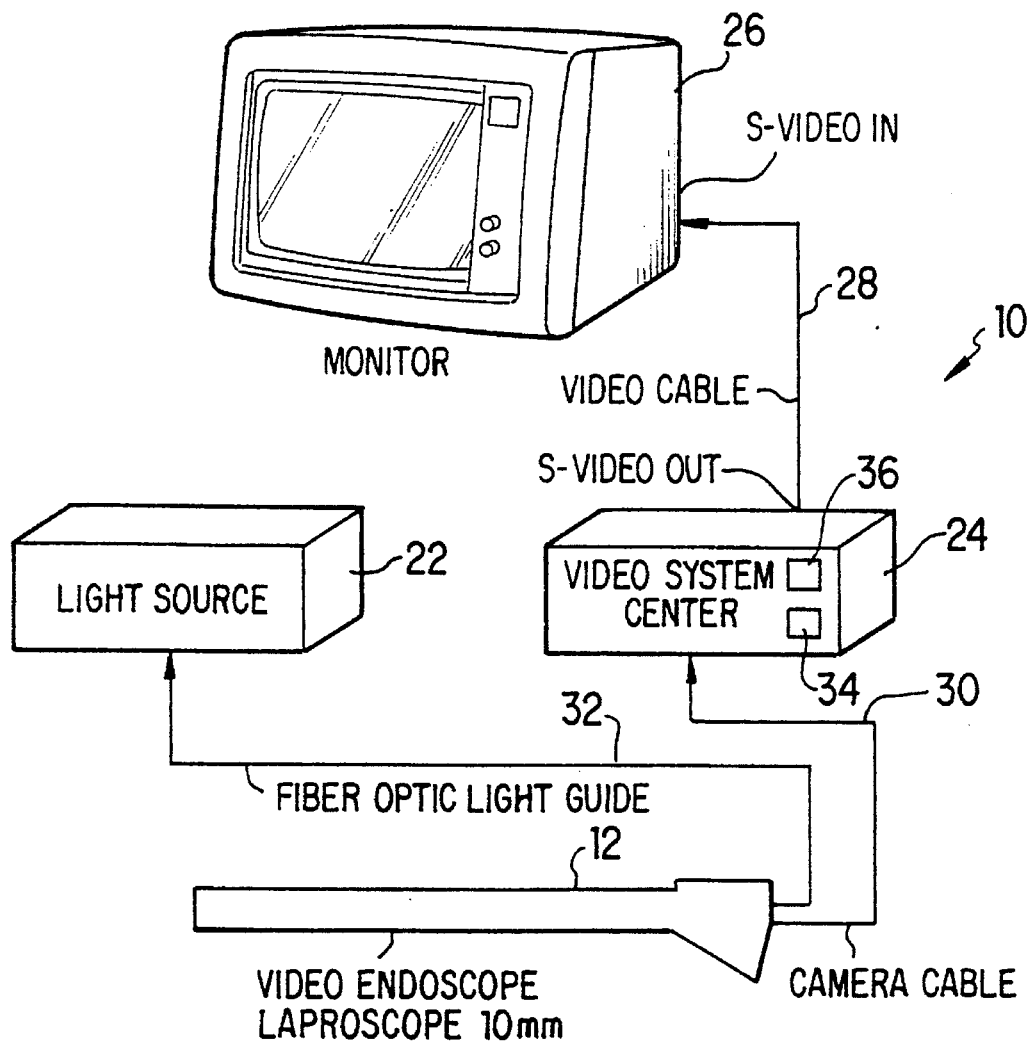
FIG. 1 is a diagram illustrating the major components of the present invention.
Figure 2:
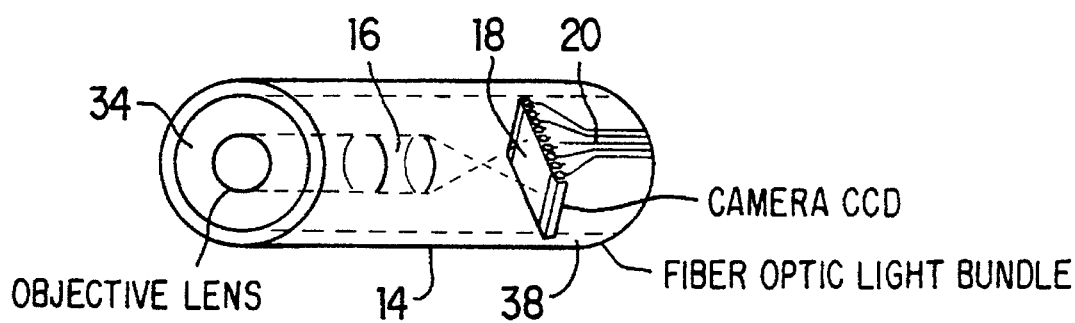
FIG. 2 is a diagram illustrating the distal end of the endoscope of the present invention.

The general system of the present invention 10 is illustrated in FIGS. 1 and 2. These figures show an endoscope 12 having a distal end 14. A rigid endoscope is shown in these figures, but it should be noted that the present invention could also include the use of a flexible endoscope. The distal portion 14 of the endoscope 12 includes an objective lens combination 16 provided between a cover glass 34 and a CCD color chip 18. Although the particular color CCD is not important, it is noted that the present invention works particularly well utilizing a CCD color chip and processing circuit designated as Panasonic Model No. GP-KS 202. This CCD color chip consists of a large number of solid state image pickup devices which convert a picture signal, at each point on the CCD based upon the brightness which is sensed at that point, directly to a chromatic output. These chromatic output signals are transferred to a video system center 24 by wires 20 provided within the endoscope 12 and by a cable 30. Although a number of different controls could be associated with the video system center 24, the system presently contemplates the use of an on/off button 34, as well as an automatic or manual light balance control 36. The present CCD color chip which is utilized, produces an analog signal which is transmitted to the video system center 24 provided with a number of processing circuits for converting the analog signals into digital signals and then back to analog signals before they are transmitted to a standard monitor 26 via an electrical cable 28. However, it should be noted that the present system would operate if chromatic digital signals were directly produced by the CCD color chip 18. These digital signals would then be sent over wires 20 and cable 30 to the video system center 24. These signals would then be processed, and either analog or digital signals would be transmitted to the monitor 26 using the cable 28.

Since the present invention contemplates usage within the human body, it is necessary that the field of vision be illuminated by a standard light source 22. This light source is external to the endoscope 12 and is connected thereto by a fiber optic light guide 32 provided with a fiber optic light bundle 38 therein. As noted in FIG. 2, the fiber optic light bundle 38 surrounds the inner periphery of the endoscope 12 and extends a small distance beyond the cover glass 34.

Figure 3:
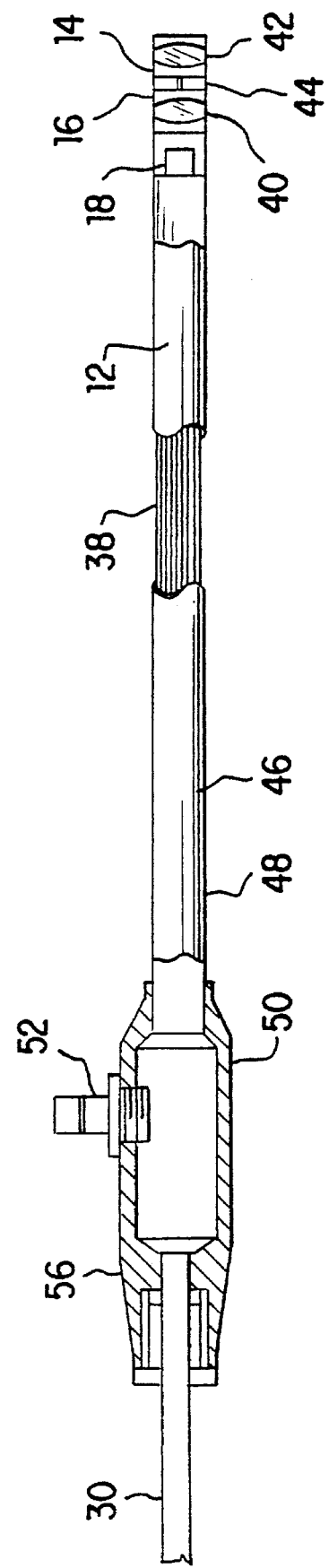
FIG. 3 is an exemplary drawing showing the endoscope of the present invention.

FIG. 3 illustrates a side view of the endoscope shown partially in sections. The distal end 14 of the endoscope is shown in slightly more detail than is illustrated in FIG. 1. The distal portion 14 includes a stand-alone lens housing section 16 provided with first and second objective lenses 40,42 separated by a lens diaphragm 44. The focal length of this lens portion of the endoscope is determined, and the opening of the aperture within the diaphragm 44 as well as the dimensions of the lenses 40 and 42, as well as their composition, are chosen accordingly. As illustrated in FIG. 2, the endoscope 12 is provided with an inner tube 46 as well as an outer tube 48. The fiber optic bundles 38 are provided between the outside surface of the inner tube 46 and the inside surface of the outer tube 48. The cable connecting the CCD color chip 18 to the video system center 24 extends through the center of the inner tube 48 and through the cable 30. The light source 22 is connected to the fiber optic light bundle 38 by a light post terminator 52 provided on the proximal end 50 of the endoscope body. A strain relief and grounding portion 56 is provided on the proximal end 50 of the endoscope 12, through which the cable 30 extends. The diameter of the outer tube is 10 mm, and the diameter of the inner tube is 8.6 mm. Therefore, the diameter of the CCD color chip 18 must be equal to or less than 8.6 mm. However, it should be noted that based upon the size of the CCD chip 18 employed, the dimension of the outer tube and the inner tube could be increased or decreased.

Figure 4:
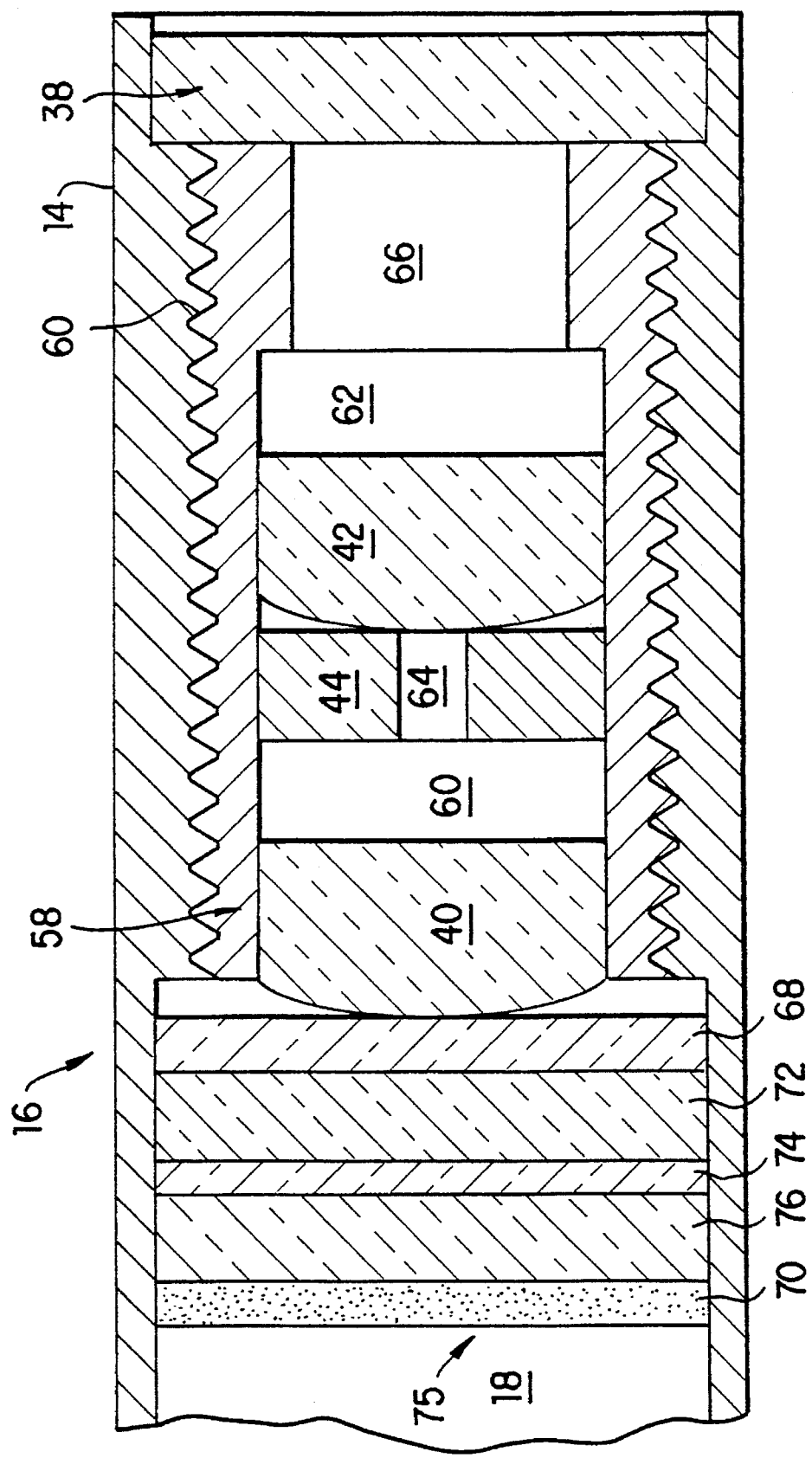
FIG. 4 is a view showing the distal end of the endoscope.

The objective lens housing 16 is shown in FIG. 4. The housing 16 is attached between the cover glass 38 and the CCD color chip 18. The housing includes lenses 40 and 42 separated from one another by a lens diagram 44 having an aperture 64 therein and a spacer element 60. The present invention utilizes a fixed focus lens which is not designed to alter its focal length once it has been installed in the endoscope and calibrated. A nut 66 is provided between the cover glass 38 and a spacer 62 provided in front of lens 42, and is used to properly position the lens housing within the endoscope. The lens housing is threaded at 60 to allow longitudinal movement of the lens housing using a special tool to turn the nut 66. A filter assembly 75 is provided between the lens assembly and is directly glued onto the CCD chip 18 by an adhesive 70. The filter 75 includes crystal filters 68, 74 and 76, as well as an infrared filter 72. After the CCD color chip 18 is affixed to the filter 75 and the lens assembly is affixed to the filter, it is slid into the endoscope from the proximal end to the distal end. At this time, the lens objective is properly positioned within the interior of the endoscope using the special tool to move the nut 66 in a longitudinal direction. Finally, the cover glass 38 is glued to the housing.

Figure 5:
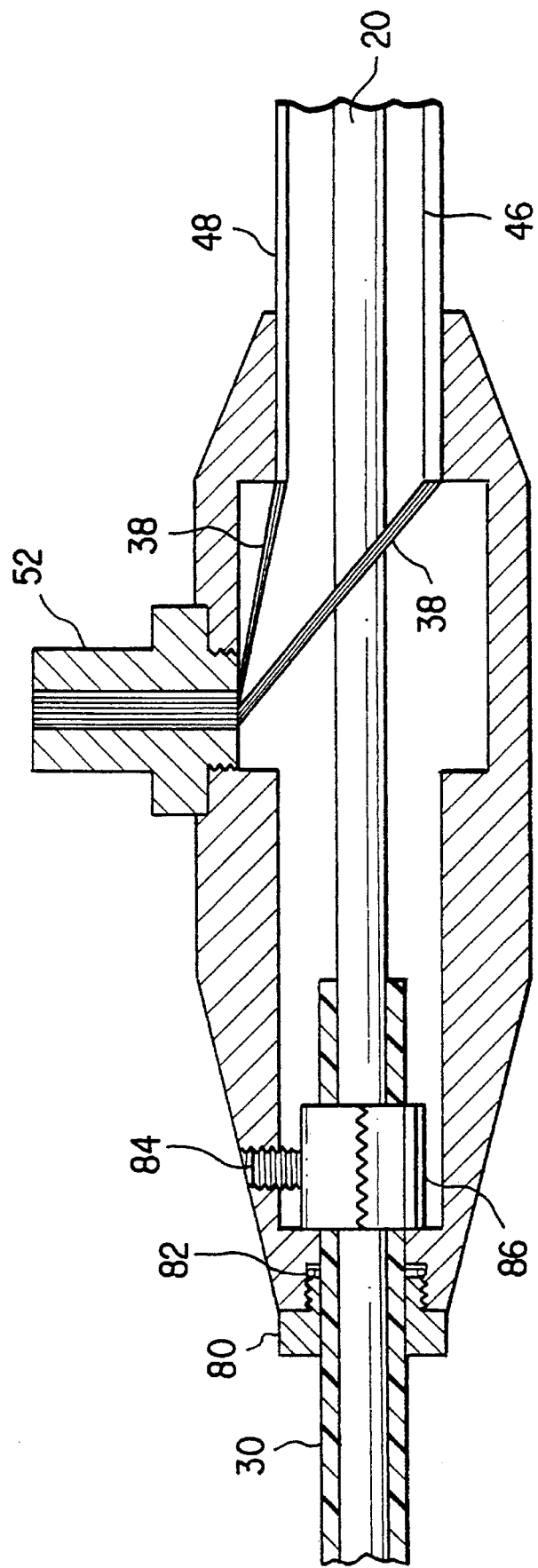
FIG. 5 is a view showing the connection of the proximal end of the endoscope to the light source and the video system center.

FIG. 5 illustrates the proximal end 50 of the endoscope. The light fibers 38 which extend between the outer periphery of the inner tube 46 and the inner periphery of the outer tube 48, pass through the light post termination section 52 and are connected to the light source 22 using the fiber optic light guide 32. A strain relief nut 80 and 0-ring 82 are included for stability. A grounding set screw 84 and brass clip ring 86 are employed to protect against interference of the signal produced by the CCD chip 18.

The entire endoscope 12 as well as the cable 30 are manufactured from materials which allow them to be sterilized by soaking them in a solution of Cidex. For this purpose, a silicon sheath is provided over the cable 30.

While the present invention has been described particularly with use as an endoscope, it is obvious that the present invention could be utilized in any application in which a color output is required from a scene provided in a very small space. Furthermore, it is believed that many additional modifications can be made which would be in the purview of one possessing ordinary skill in the art.

What is claimed is:

1. An endoscope for viewing a scene, within the body of a human or an animal, comprising an elongated tube having distal and proximal ends, the diameter of said elongated tube being equal to or less than 10 mm;

an objective lens system provided in said distal end of said elongated tube, said objective lens system comprising first and second lenses, a lens diaphragm having an aperture therein, said lens diaphragm provided between said first and second lenses, a first spacer provided in front of said first lens, a second spacer provided between said lens diaphragm and said second lens;

a nut provided in front of said first spacer for positioning said objective lens system; and a color charge coupled device having a diameter equal to or less than 8.6 mm provided in said distal end of said elongated tube behind said objective lens system, said charge coupled device directly providing a chromatic signal based upon the viewed scene, said charge coupled device connected to one or more electrical wires for transmitting said chromatic signal from said distal end of said elongated tube to said proximal end of said elongated tube.

2. The endoscope in accordance with claim 1, further including a filter assembly provided between said objective lens system and said color charge coupled device, said filter assembly including three crystal filters and an infrared filter.

3. The endoscope in accordance with claim 1, further including an inner tube provided within and extending the entire length of said elongated tube, and a fiber optic bundle provided between said inner tube and said elongated tube, said fiber optic bundle extending from said distal end of said elongated tube to said proximal end of said elongated tube.

4. An endoscopic system for viewing a scene within the body of a human or an animal, comprising, an elongated tube having distal and proximal ends, the diameter of said elongated tube being equal to or less than 10 mm;

an objective lens system provided in said distal end of said elongated tube; said objective lens system comprising first and second lenses, a lens diaphragm having an operative therein, said lens diaphragm provided between said first and second lenses, a first spacer provided in front of said first lens, a second spacer provided between said lens diaphragm and said second lens;

a nut provided in front of said first spacer for positioning said objective lens system;

a color charge coupled device having a diameter being equal to or less than 8.6 mm provided in said distal end of said elongated tube behind said objective lens system, said charge coupled device directly providing a chromatic signal based upon the viewed scene, said charge coupled device connected to one or more electrical wires for transmitting said chromatic signal from said distal end of said tube to said proximal end of said tube;

a chromatic signal processing circuit connected to said one or more electrical wires and provided external to said elongated tube; and a monitor connected to said chromatic signal processing circuit for viewing the scene.

5. The endoscopic system in accordance with claim 6, further including a filter assembly provided between said objective lens system and said color charge coupled device, said filter assembly including three crystal filters and an infrared filter.

6. The endoscopic system in accordance with claim 4, further including an inner tube provided within and extending the entire length of said elongated tube, and a fiber optic bundle provided between said inner tube and said elongated tube, said fiber optic bundle extending from said distal end of said elongated tube to said proximal end of said elongated tube, and a light source connected to said fiber optic bundle extending from the proximal end of said elongated tube, said light source provided external to said elongated tube.

7. The endoscopic system in accordance with claim 4, further including a filter assembly provided between said objective lens system and said color charge coupled device, said filter assembly including three crystal filters and an infrared filter.

\* \* \* \* \*